(12) United States Patent
Baldauf et al.

(10) Patent No.: US 8,900,690 B2
(45) Date of Patent: Dec. 2, 2014

(54) LAMINATE

(75) Inventors: Georg Baldauf, Laer (DE); Dieter Homoelle, Ochtrup (DE); Marcus Schoenbeck, Versmold (DE)

(73) Assignee: Mondi Consumer Packaging Technologies GmbH, Gronau (DE)

( * ) Notice: Subject to any disclaimer, the term of this patent is extended or adjusted under 35 U.S.C. 154(b) by 972 days.

(21) Appl. No.: 12/632,333

(22) Filed: Dec. 7, 2009

(65) Prior Publication Data
US 2010/0143670 A1 Jun. 10, 2010

(30) Foreign Application Priority Data
Dec. 6, 2008 (DE) .................. 20 2008 016 226 U

(51) Int. Cl.
B32B 3/10 (2006.01)
A61F 13/56 (2006.01)
B32B 5/04 (2006.01)
B32B 5/26 (2006.01)
B32B 27/12 (2006.01)

(52) U.S. Cl.
CPC . *A61F 13/56* (2013.01); *B32B 5/04* (2013.01); *B32B 5/26* (2013.01); *B32B 27/12* (2013.01)
USPC .................. 428/196; 428/201; 428/203

(58) Field of Classification Search
USPC .................................. 428/196, 201, 203
See application file for complete search history.

(56) References Cited

U.S. PATENT DOCUMENTS

| 7,470,340 | B2 | 12/2008 | Baldauf | 156/73.1 |
| 2006/0069361 | A1* | 3/2006 | Olson | 604/361 |
| 2008/0108267 | A1* | 5/2008 | Baldauf et al. | 442/381 |
| 2009/0068393 | A1* | 3/2009 | Homolle et al. | 428/99 |

* cited by examiner

Primary Examiner — Bruce H Hess
Assistant Examiner — Christopher Polley
(74) Attorney, Agent, or Firm — Andrew Wilford

(57) ABSTRACT

A laminate for making a flexible fastener. The laminate has according to the invention outer layers of nonwoven and parallel and spaced strips of an elastic film laminated between the outer layers. The outer layers are directly bonded to each other in regions between the elastic strips and there form inelastic regions of the laminate while regions each containing one of the strips form elastic regions. At least one of the outer layers is a sheer nonwoven. A color or pattern imprint is printed on the one outer layer over the elastic and inelastic regions.

6 Claims, 2 Drawing Sheets

LAMINATE

FIELD OF THE INVENTION

The invention relates to a composite material in particular for making flexible diaper fasteners. The laminate has outer layers of nonwoven and parallel strips of an elastic film laminated between the outer layers. The outer layers are thereby directly connected to one another in regions between the elastic strips. These regions form inelastic regions of the laminate. Moreover, the regions of the laminate each containing one of the strips form elastic regions.

BACKGROUND OF THE INVENTION

A generic laminate is known from U.S. Pat. No. 7,470,340. The laminate formed in the method described there has elastic and inelastic regions, parallel strips of elastic laminate being laminated between two webs of nonwoven material at a spacing from one another. The disadvantage with the laminate described there is that the elastic regions have a different transparency from the inelastic regions. When the laminate is used, for example, in a baby diaper, the elastic regions thus appear lighter than the inelastic regions. In this manner the impression is given that the laminate, which is the visible component of a diaper closure, has been produced from non-uniform materials. The user of the diaper closure may draw the conclusion from this that the fastener is unstable, which means that the user judges the diaper closure overall to be substandard.

OBJECTS OF THE INVENTION

It is therefore an object of the present invention to provide an improved laminate.

Another object is the provision of such an improved laminate that overcomes the above-given disadvantages, in particular that leaves the user with the impression that the laminate was produced uniformly.

SUMMARY OF THE INVENTION

A laminate for making a flexible fastener. The laminate has according to the invention outer layers of nonwoven and parallel and spaced strips of an elastic film laminated between the outer layers. The outer layers are directly bonded to each other in regions between the elastic strips and there form inelastic regions of the laminate while regions each containing one of the strips form elastic regions. At least one of the outer layers is a sheer nonwoven. A color or pattern imprint is printed on the one outer layer over the elastic and inelastic regions.

This imprint reduces the difference in the transparency between elastic and inelastic region of the laminate. Both regions are less sheer and the user of the laminate is given the impression that it has not been produced by joining together material components of different types. The uniform appearance is intensified in particular when the laminate is printed with a pattern. Optical matching of elastic and inelastic regions of the laminate inspires greater confidence in the user in the durability and in the qualitative composition of the laminate. The materials used can be, e.g. a graded nonwoven with a mass per unit area of 20 to 35 g/m$^2$ (gram per square meter) or a multilayer nonwoven. A multilayer nonwoven with a layer of melt-blown nonwoven between two layers of spun-bond nonwoven is particularly suitable. This material, referred to as SMS nonwoven, preferably has a mass per unit area between 10 and 30 g/m$^2$. The film laminated in the elastic regions can have a thickness of 20 to 120 μm. Lamination of the nonwoven with the elastic film can preferably be carried out with a hot melt laminating method.

In a preferred embodiment of the laminate the imprint can comprise a pattern of stripes or wavy lines that extend transversely to the stretch direction of the laminate. It is advantageous with this type of embodiment of the pattern that the pattern also is preserved as a recognizable pattern when the laminate is stretched. Furthermore, for example, a striped or wave-shaped form of the pattern gives the user the option, for example, to always stretch a diaper closure by the same amount because the user remembers the form of the pattern changed by stretching. A pattern of this type thus indirectly forms a scale for stretching. Accordingly, in principle that waves or stripes can be provided that in the unstretched state have a different spacing and/or different extensions in the direction of stretching in the elastic regions on the one hand and in the inelastic regions on the other hand, so that a uniform pattern is not formed until an extension preferred for use has been reached.

In a further embodiment of the laminate, furthermore, the imprint can be arranged on the inner face of the nonwoven layer. This arrangement of the imprint makes it possible to prevent constituents of the printing material, such as for example ink when the laminate is used for a diaper closure, from coming into contact with the skin of the wearer of the diaper. This can be advantageous in particular in preventing undesirable skin irritation.

Another embodiment of the laminate provides that the imprint is on a pretreated surface of the non-woven layer. The pretreatment of the area thereby comprises an application of a nonwoven fabric primer to which largely prevent ink from bleeding through the nonwoven. This provides an advantage in particular in the production of the laminate according to the invention, in that the machine that produces the laminate is less soiled or not soiled at all by preventing the ink from bleeding through. The production process can also be thus carried out in an accelerated manner. Furthermore, the imprint can comprise a printed image applied to the nonwoven layer in a gravure printing process.

Solvent-based, water-based or also UV-curing printing inks can be used to produce the printed image. In particular the printing ink for the imprint can be based on a polyvinyl butyral (PVB), a cellulose nitrate (NC) or on a mixture of cellulose nitrate and polyamide (NC/PA) and preferably is mixed with an adhesive resin. The printing can thereby be carried out inline, that is, the laminate is first printed, then the strips are cut and subsequently a three-layer strip hot-melt lamination is effected. In the manufacture of the laminate according to the invention, the printing accordingly represents an additional process step that is easy to integrate into the overall production process.

Furthermore, with the laminate according to the invention the elastic regions of the laminate are mechanically activated by overstretching, the outer layer having preferably been printed before mechanical activation. This mechanical activation entails a partial tearing of the inelastic outer layers so that the laminate is easy to stretch in the elastic regions.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
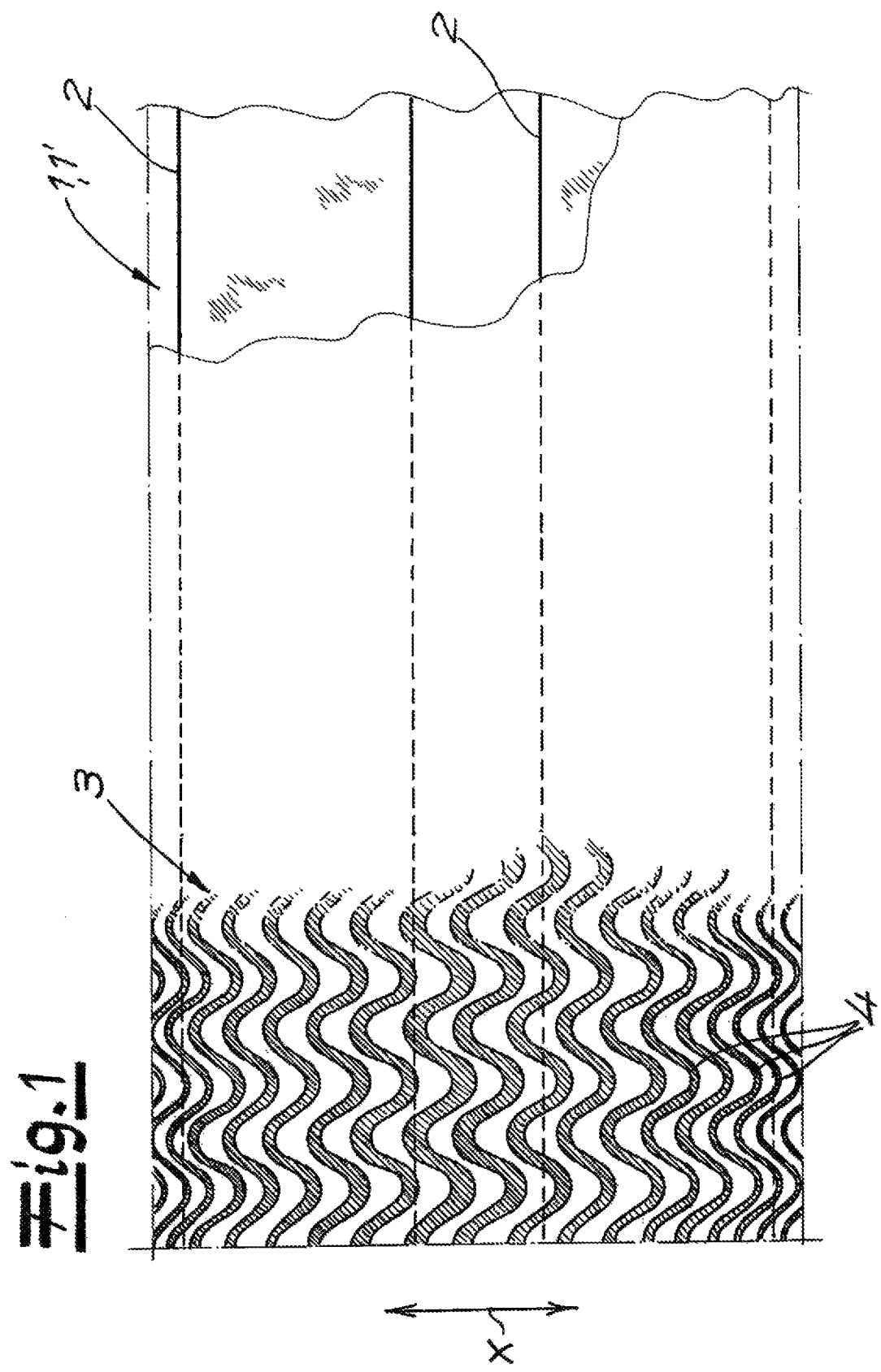
FIG. 1 is a top view of a piece of the laminate.

As seen in FIG. 1 a laminate, in particular for making flexible diaper fasteners, has outer layers 1 and 1' of nonwoven and parallel spaced strips 2 of an elastic film laminated between the outer layers 1 and 1'. The outer layers 1 and 1' are here directly connected to one another in the regions between the elastic strips 2. They form inelastic regions of the laminate. Regions of the laminate each containing one strip 2 thereby form the elastic regions. FIG. 1 shows that at least one of the outer layers 1 and 1', which is a sheer nonwoven, is printed in color with an imprint 3 extending over the elastic and the inelastic regions. According to the embodiment shown, one of the outer layers 1 and 1' has an imprint 3 in the form of a pattern. Through this pattern, the elastic and inelastic regions appear more similar to one another. A difference in terms of transparency or optical appearance is reduced. As can be seen from FIG. 1, the pattern is composed of wavy lines 4 that extend transversely to the stretch direction x of the laminate. Alternatively thereto, a striped or dotted pattern can be provided. Since the pattern extends transverse to the stretch direction x of the material, the design or the form of the pattern is also essentially preserved after the laminate has been stretched. A wavy pattern distorted by stretching in one of the elastic regions differs only slightly from the wavy pattern of the inelastic, inextensible region of the laminate. With the embodiment of the laminate according to the invention shown in FIG. 1, it can also be advantageous when the imprint 3 is on the inner face of the outer layer 1, which is above the strips 2 when the laminate is used as part of a fastener.

Figure 2:
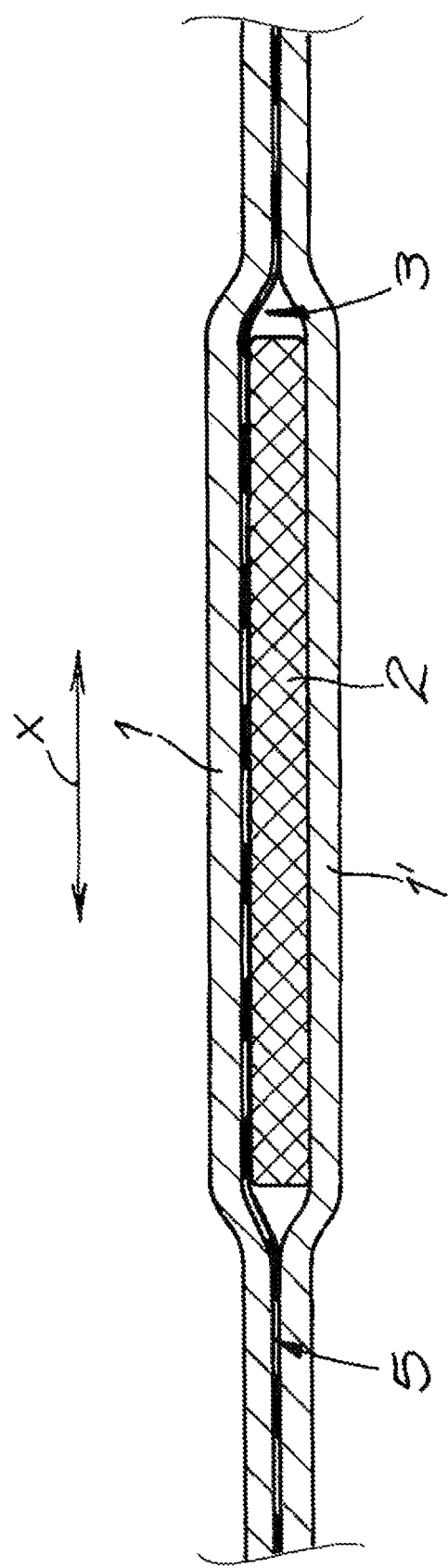
FIG. 2 is a vertical section through the laminate.

FIG. 2 shows a vertical section through the laminate according to the invention along the stretch direction x, with the imprint 3 on a pretreated area 5 of the upper outer layer 1 on the inner face shown in FIG. 2 and where the pretreatment entail the application of a nonwoven fabric primer that largely prevents ink from bleeding through the nonwoven. Furthermore, the imprint 3 can comprise a printed image applied to the nonwoven layer in a gravure printing process. The printing ink for the imprint 3 can thereby be based on a polyvinyl butyral (PVB), cellulose nitrate (NC) or a mixture of cellulose nitrate and polyamide (NC/PA). Preferably the printing ink can be mixed with an adhesive resin. Furthermore, the elastic regions of the laminate can also be mechanically activated by overstretching, the outer layer 1 having been printed before the mechanical activation

We claim:

1. A laminate for making a flexible fastener, the laminate comprising:

outer layers of nonwoven of which one is sheer;

parallel and spaced strips of an elastic film laminated between confronting inner faces of the outer layers and there forming elastic regions, the outer layers being directly bonded to each other between the elastic strips and there forming inelastic regions alternating with the elastic regions each containing one of the elastic-film strips; and a color or pattern imprint on the inner face of the one sheer outer layer over the elastic regions and the inelastic regions, visible through the one sheer outer layer by a user of the laminate, and formed by wavy lines extending transversely to a stretch direction of the laminate.

2. The laminate defined in claim 1, further comprising a layer of nonwoven fabric primer between a surface of the one sheer layer and the color or pattern imprint.

3. The laminate defined in claim 1 wherein the color or pattern imprint is a printed image applied in a gravure printing process.

4. The laminate defined in claim 1 wherein the color or pattern imprint is formed by an ink based on a polyvinyl butyral, a cellulose nitrate, or a mixture of cellulose nitrate and polyamide.

5. The laminate defined in claim 1 wherein the elastic regions of the laminate are mechanically activated by overstretching, at least the one outer sheer layer having been printed with the color or pattern imprint before mechanical activation.

6. A laminate for making a flexible fastener, the laminate comprising:

outer layers of nonwoven of which one is sheer;

parallel and spaced strips of an elastic film laminated between confronting inner faces of the outer layers and there forming elastic regions, the outer layers being directly bonded to each other in regions between the elastic strips and there forming inelastic regions of the laminate alternating with the elastic regions each containing one of the strips; and a color or pattern imprint on the inner face of the one sheer outer layer over the elastic and inelastic regions visible through the one sheer outer layer by a user of the laminate and formed by wavy lines extending transversely to a stretch direction of the laminate across the elastic and inelastic regions, the wavy lines having in an unstretched state a nonuniform spacing or extension in the stretch direction that is only rendered uniform when the laminate is stretched in the direction by a preferred extent.

* * * * *